United States Patent [19]

Senelonge

[11] 4,135,561
[45] Jan. 23, 1979

[54] MACHINE FOR INTRODUCING MEASURED AMOUNTS OF LIQUIDS INTO VIALS AND OTHER RECEPTACLES

[76] Inventor: Henri Senelonge, Rue de la Charmette, Lagnieu, Ain, France

[21] Appl. No.: 817,427

[22] Filed: Jul. 20, 1977

[30] Foreign Application Priority Data

Jul. 20, 1976 [FR] France .................. 76 22786

[51] Int. Cl.² .................................... B65B 3/04
[52] U.S. Cl. .................................. 141/234
[58] Field of Search ............. 141/82, 100, 231, 232, 141/234, 237, 238, 240, 242, 243, 244, 18, 329, 330, DIG. 1; 222/146 H, 255; 417/271

[56] References Cited

U.S. PATENT DOCUMENTS 3,939,883  2/1976  Harrell et al. .................. 141/231

Primary Examiner—Houston S. Bell
Attorney, Agent, or Firm—Karl F. Ross

[57] ABSTRACT

A generally vertical frame has a pair of columns on which an upper support and a lower support are slidably mounted, the lower support carrying the barrels of a row of syringes whose plungers are fastened to the upper support. The latter support can be alternately lowered and raised, manually by a lever or automatically by a cam, and is connected with the lower support by a lost-motion linkage allowing the two supports to be separated to an extent sufficient for a partial withdrawal of the plungers from their barrels when the syringes are dipped into one or more supply containers on a base onto which the lower support is held by a strong magnetic coupling until entrained by the rising upper support. Upon alignment of the elevated syringes with a row of receptacles to be filled, an interposed stop arrests their barrels while the plungers descend with the lower support to expel the previously aspirated liquids until the two supports come into contact with each other, whereupon a weaker magnetic coupling therebetween causes their joint ascent preparatorily to the next syringe-refilling operation. The frame may be swingable about a horizontal axis for alternate alignment of the syringes with the supply containers and the receptacles which can be arrayed in one or more rows.

15 Claims, 9 Drawing Figures

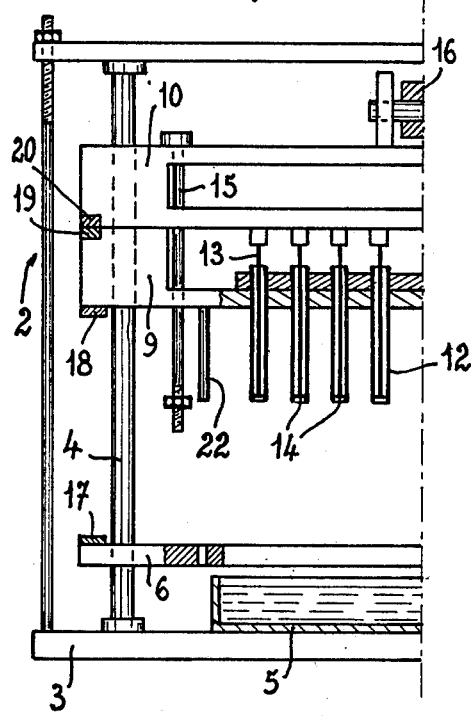
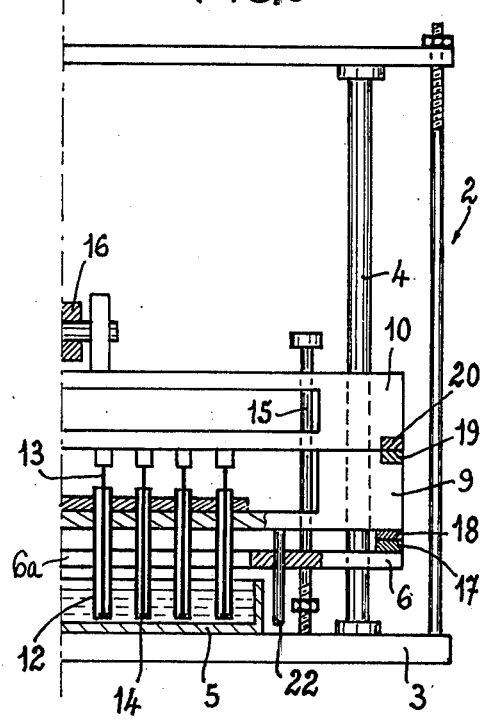
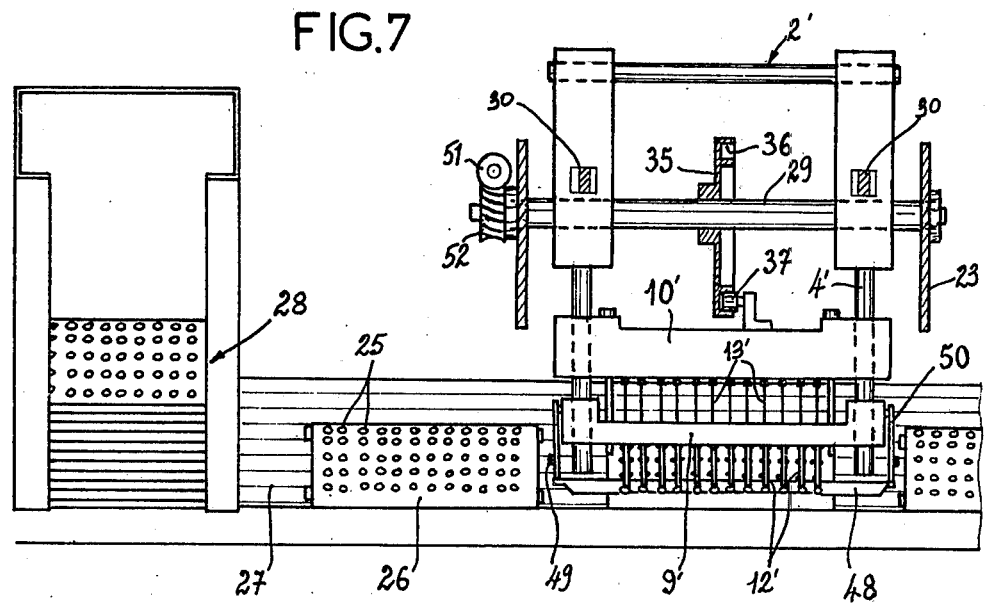

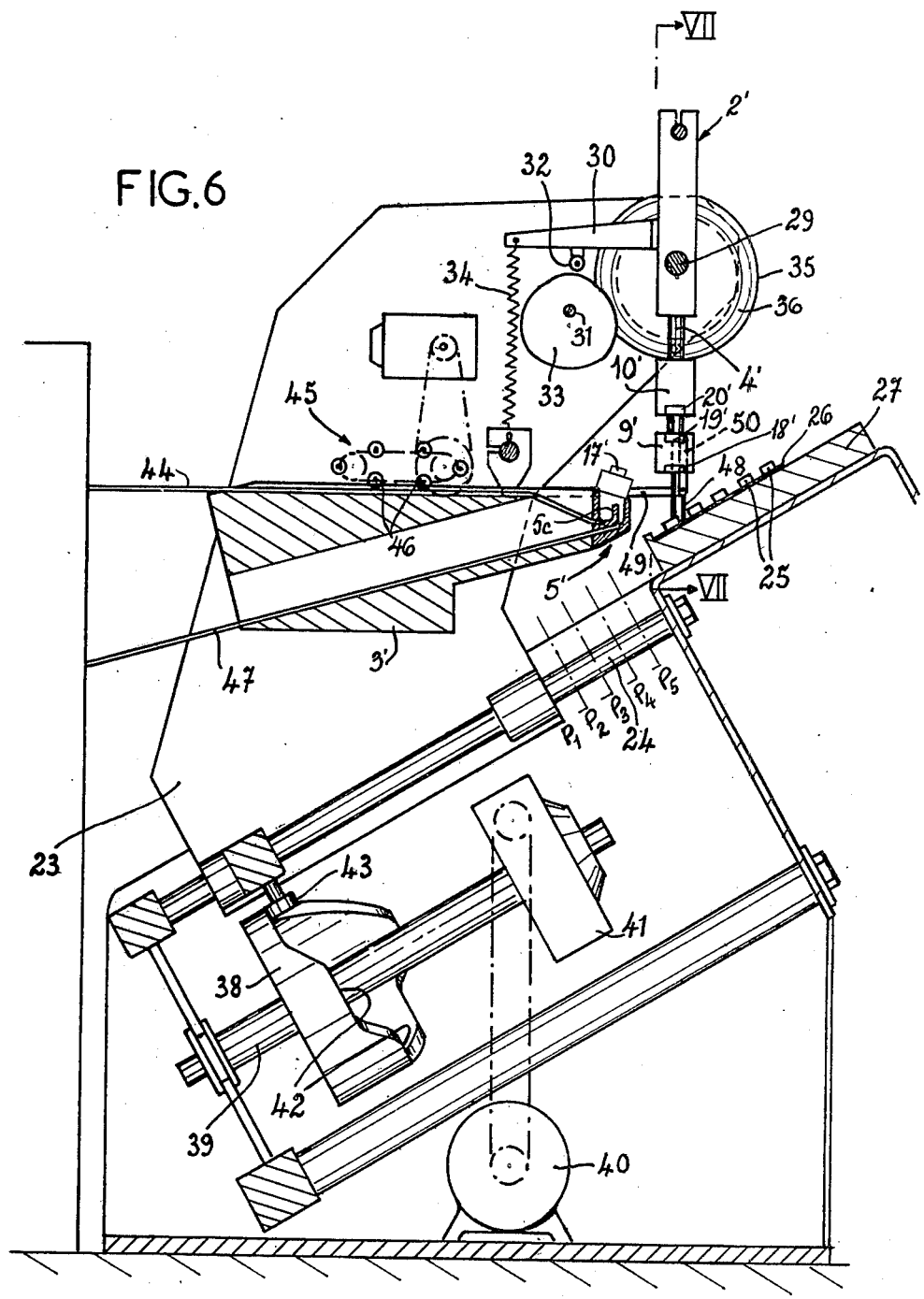

MACHINE FOR INTRODUCING MEASURED AMOUNTS OF LIQUIDS INTO VIALS AND OTHER RECEPTACLES

FIELD OF THE INVENTION

My present invention relates to a machine for introducing measured amounts of liquids into vials, test tubes or other receptacles, particularly but not exclusively for use in the chemical, pharmaceutical or bacteriological field.

BACKGROUND OF THE INVENTION

The transfer of a certain volume of liquid from a supply container to a receptacle with the aid of a manually operated syringe is a painstaking and time-consuming operation, especially when a large number of such receptacles have to be filled with different liquids. In many instances the receptacles are simple depressions in a common matrix such as a sheet or plate of resinous material; filling these inseparable receptacles one by one may result in an excessive lengthening of the storage time of some of the liquids, leading to undesirable reactions.

OBJECTS OF THE INVENTION

The general object of my present invention, therefore, is to provide a machine for automatically or semi-automatically dispensing the liquids in precisely dosed amounts to such receptacles in an efficient and economical manner.

A related object is to provide a machine of this type capable of filling a large number of such receptacles simultaneously.

SUMMARY OF THE INVENTION

These objects are realized, pursuant to my present invention, by the provision of a mounting such as a two-column frame rising above a base which carries one or more containers filled with a supply of a single liquid or several liquids to be dispensed, an upper support and a lower support being guided on this mounting for generally vertical reciprocation with the aid of manually or automatically actuated operating means such as a lever or a cam. A set of horizontally spaced-apart syringes, equal in number to a set of receptacles to be filled simultaneously, have bodies or barrels carried on the lower support while their plungers are carried on the upper one, the two supports being interconnected by a lost-motion linkage which allows them to be separated to a preferably adjustable extent sufficient for a partial withdrawal of the plungers from their barrels. When the plungers are fully inserted into the barrels, the two supports are in contact with each other and are releasably held together by first retaining means whose action can be overridden by second retaining means provided on the lower support and on the base, the latter retaining means becoming effective when the two supports descend into a bottom position in which the barrels dip into the container or containers for the purpose of refilling. Thus, upon the next ascending stroke of the support, the lower support with its syringe barrels remains initially stationary so that liquid is aspirated into the barrels by the withdrawing plungers. When the maximum separation of the supports allowed by the lost-motion linkage is reached, the lower support is entrained upwardly as the upper support continues to rise toward its top position. With the syringe barrels thus elevated above the supply container or containers, a holder carrying the receptacles to be filled can be aligned therewith; upon the following descent of the two interlinked supports, the lower support is kept elevated by previously inactive stop means so that the contents of the syringe barrels are discharged by the descending plungers into the receptacles aligned therewith.

Advantageously, the first and second release means referred to above are constituted by passive elements requiring no control signals for their activation or deactivation. In a preferred embodiment, these passive elements are a relatively weak magnetic coupling between the upper and lower supports and a relatively strong magnetic coupling between the lower support and the base.

The alignment of the syringe barrels with the receptacles to be filled can be carried out in either of two ways, i.e. by interposition of their holder between the base and the lower support or by a displacement of that support between a position of alignment with the supply container (or containers) and a position of alignment with the receptacles. The latter solution is particularly suitable for a fully automated system in which the holder for the receptacles includes a transporter such as an endless web intermittently advancing a succession of plates or trays, each forming or carrying an array of integrated receptacles, past a filling station.

If the receptacles are arrayed in several parallel rows, the mounting frame for the reciprocable supports may be pivotally secured to a carriage for swinging about an axis parallel to these rows between a replenishing position and a dispensing position; after each dispensing or replenishing operation, the carriage is advanced in a direction perpendicular to the axis to align the refilled syringe barrels successively with the several rows of receptacles of a given tray until the entire array is filled with liquid.

BRIEF DESCRIPTION OF THE DRAWING

The above and other features of my invention will now be described in detail with reference to the accompanying drawing in which:

FIGS. 2-5 are partial elevational views of the same machine in different phases of operation;

FIG. 6 is a cross-sectional view of a machine representing a fully automated embodiment of my invention;

FIG. 7 is an elevational view taken in part on the line VII — VII of FIG. 6 and showing other components of the automatic system.

SPECIFIC DESCRIPTION

Figure 1:
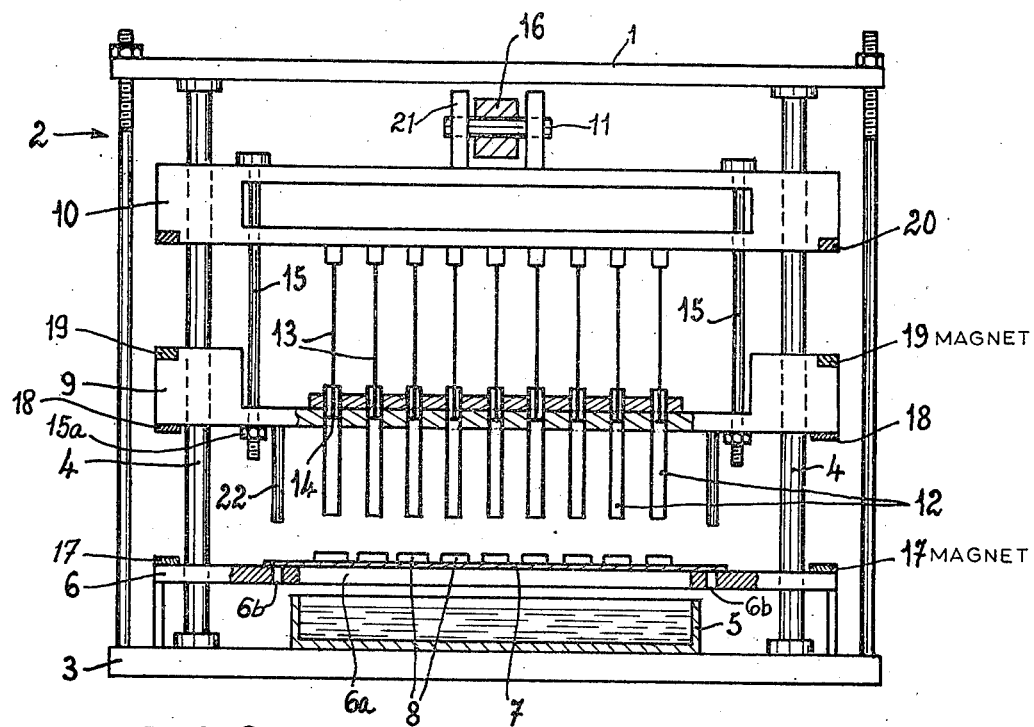
FIG. 1 is an elevational view (partly in section) of a liquid-dispensing machine according to my invention, shown in one phase of operation.
Figure 2:
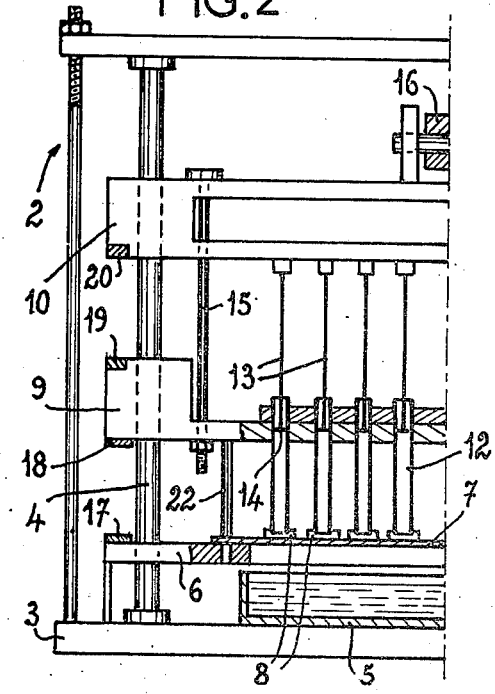
Figure 3:
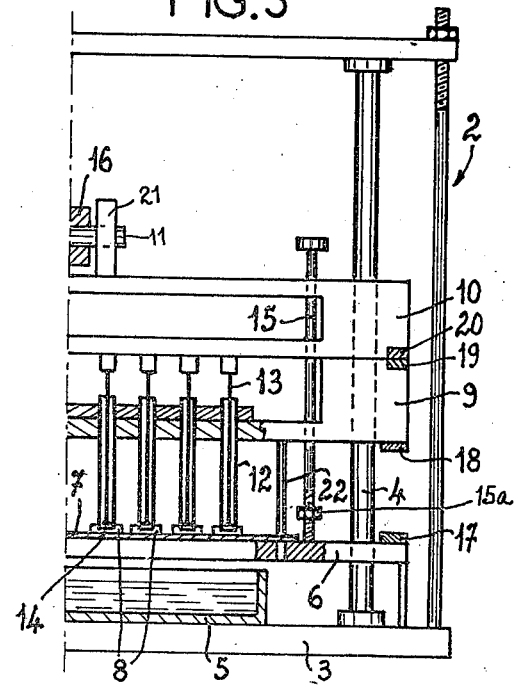

The machine shown in FIGS. 1-5 comprises a stationary frame 2 including a base 3 and a top 1 interconnected by a pair of vertical columns 4 serving as guides for the reciprocation of two beam-shaped supports, i.e. a lower support 9 and an upper support 10. A row of shallow vessels 8, constituting a set of receptacles to be filled with liquid from a supply container 5 on base 3, are carried on a holder in the form of a plate 7 which in FIGS. 1-3 is positioned on a platform 6 fixedly secured to the base above container 5. Platform 6 has a slot 6a overlying the container 5 and further has a pair of bores 6b flanking that slot.

A set of syringes, whose number corresponds to that of the receptacles 8 to be filled, have barrels 12 mounted in support 9 and plunger heads 14 with stems 13 carried on support 10.

The syringe barrels 12 are aligned with slot 6a so as to be able to dip into the container 5 upon removal of the receptacle holder 7 as partly illustrated in FIG. 5. Although only a single container 5 has been shown, it will be understood that the same could be subdivided into a plurality of compartments, designed to store different liquids for respective syringes or groups of syringes, or replaced by as many individual containers. The storage capacity of the container or containers should in any event be substantially greater than that of the respective syringe or syringes so that each syringe can be refilled a number of times.

Support 9 is provided with a pair of depending pins 22, of a length slightly exceeding that of the projecting sections of syringe barrels 12, which fit into the holes 6b of platform 6 but are prevented from entering these holes by the overlying plate 7 in the positions shown in FIGS. 1–3. The supports 9 and 10 are interconnected by a lost-motion linkage comprising a pair of threaded vertical rods 15 traversing these supports, each rod being engaged by a nut 15a whose position determines the maximum distance by which the two supports can be separated as illustrated in FIGS. 1 and 2. Naturally, the nuts 15a can be secured in their selected positions of adjustment by non-illustrated counternuts or the like.

In their contacting position, illustrated in FIGS. 3–5, the supports 9 and 10 are releasably held together by retaining means in the form of a pair of relatively weak permanent magnets 19 on support 9 coacting with ferromagnetic armatures 20 on support 10. Similar but stronger magnets 17 on platform 6, coacting with ferromagnetic armatures 18 on the underside of support 9, serve as retaining means for releasably immobilizing that support with reference to base 3 in its bottom position illustrated in FIG. 5. Support 10 can be vertically reciprocated by a manually operated lever 16, swingable about a fixed fulcrum not shown, having an extremity articulated to that support by a shaft 11 mounted in lugs 21.

At the beginning of an operating cycle, the supports 9 and 10 are in the position of FIG. 5 in which the lower ends of barrels 12 are immersed in the liquid of container 5 and are flush with the plunger heads 14, the armatures 18 and 20 of the two magnetic couplings being both in contact with their magnets 17 and 19. The stronger coupling 17, 18, however, overrides the coupling 19, 20 so that support 9 remains in place when support 10 is subsequently elevated by means of lever 16, thereby allowing the plungers to rise in their barrels and to aspirate measured amounts of liquid. When the upper support 10 begins to entrain the lower support 9 via lost-motion linkage 15, 15a, the filled syringe barrels 12 are extracted from the container 5 and elevated above the platform 6 as seen in FIG. 1. The holder 7 with its receptacles 8 can now be positioned on platform 6 whereupon the two supports 9, 10 are jointly lowered until the pins 22 come to rest on the plate 7 now obstructing the holes 6b, thereby stopping the further downward movement of the syringe barrels just as they are about to enter the respective receptacles 8. This has been illustrated in FIG. 2. The upper support 10 then continues its descent until it comes to rest on the lower support 9 as shown in FIG. 3, the plunger heads 14 then reaching the lower ends of the barrels 12 so that the entire contents thereof are discharged into the associated receptacles. Next, as shown in FIG. 4, the upper support 10 is elevated and entrains the lower support 9 with the aid of magnetic coupling 19, 20 inasmuch as the coupling 17, 18 is ineffectual in the position of FIG. 3. Following removal of plate 7 with the filled receptacles, another cycle can be started with a replenishing operation in the position of FIG. 5.

In FIGS. 6–9, in which elements analogous to those of the preceding Figures have been identified by corresponding reference numerals supplemented by a prime mark, supports 9', 10' are reciprocable on columns 4' of a mounting frame 2' which is freely swingable about a horizontal shaft 29 journaled in a carriage 23. This carriage, riding on a pair of inclined rails 24 (only one shown), has a base 3' supporting a supply container (or group of containers) 5' to which liquid is continuously fed from a nonillustrated source, such as a large-capacity reservoir, via a conduit (or group of conduits) 44 designed at least in part as an upwardly open channel along which the liquid is impelled by a pump 45 shown as a motor-driven endless conveyor chain with rollers 46 sweeping the channel bottom. The feed rate of pump 45 should exceed the rate at which the liquid is dispensed by the apparatus, also taking into account possible evaporation losses, so that a main compartment 5a (see FIG. 8) of container 5' is always filled to the edge of an internal partition 5c, the excess passing into an overflow compartment 5b whence a drain 47 returns it to the source.

Figure 8:
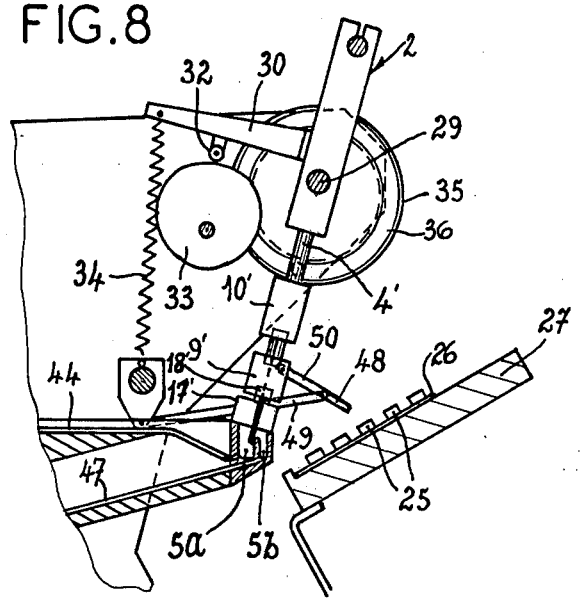
FIGS. 8 and 9 are fragmentary cross-sectional views of the machine shown in FIG. 6, illustrating other phases of operation thereof.
Figure 9:
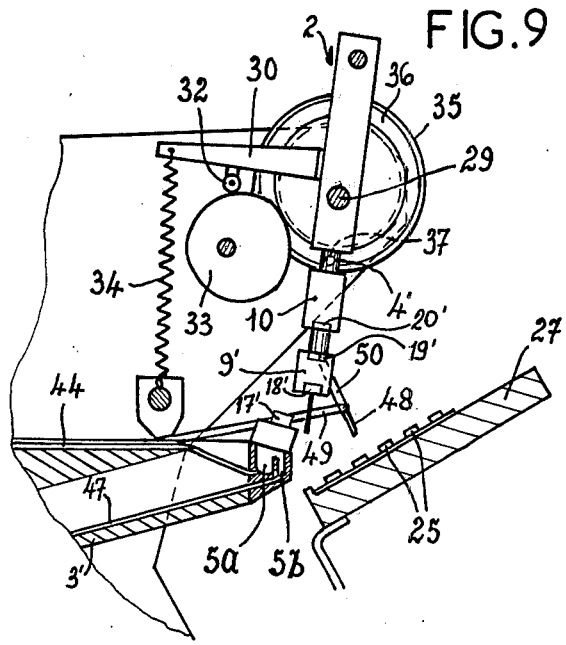

The receptacles to be filled in any operating cycle are assumed in this instance to be inseparably grouped on a common matrix 26, such as a sheet or plate of resinous material, in which they may be formed as simple depressions 25 arrayed in a plurality of rows parallel to shaft 29 as seen in FIG. 7. In FIGS. 6, 8 and 9, however, these receptacles 25 have been shown as vessels rising above the plate 26 for the sake of clarity. Under the control of a nonillustrated programmer, a number of such plates 26 are successively deposited from a hopper 28 on a transporter 27 in the form of an intermittently advancing endless web, each advance juxtaposing one plate 26 with the container or set of containers 5' of the filling station represented by carriage 23. Several such filling stations could be disposed along the transport path to supply each receptacle with two or more liquids in succession. With five rows of receptacles per plate, as shown, each machine cycle includes five dispensing operations interleaved with as many replenishing operations.

Frame 2' is rigid with a pair of levers 30 carrying rollers 32 which ride the peripheries of respective cam disks 33 on a shaft 31 driven by a motor 40 through a nonillustrated transmission allowing for a limited relative displacement of the motor and the carriage 23 on which the shaft 31 is journaled. Another part of this transmission, including a worm 51 and a worm gear 52, drives the shaft 29 to which a slave cam 35 is keyed, a roller 37 on support 10' engaging in a groove 36 of cam 35 for periodically raising and lowering this support in synchronism with the oscillation of frame 2' under the control of cam 33 onto which the cam follower 32 is biased by a tension spring 34 anchored to base 3' and lever 30. When the roller 32 rides on a high dwell of cam 33, frame 2' swings clockwise (FIG. 8) to align the syringe barrels 12' on support 9' with main compartment 5a of container 5', the cam 35 then lowering the two supports 9', 10' so that the syringes dip into the container whereupon the rise of support 10' with plunger stems 13' fills these barrels in the aforedescribed manner. With continuous rotation of cam 33, after the support 10' has entrained the support 9' upwardly through their lost-motion linkage, the frame swings counterclockwise into an intermediate position (FIG. 9) in which the syringes lie above a gap between base 3' and transport web 27; at the same time a horizontal bar 48, hinged to support 9' via arms 50 which are articulated to base 3' by links 49, is swung back from an inoperative position (FIG. 8) so as to come to rest on plate 26 behind a row of receptacles 25 when the spring 34 pulls the frame into its extreme counterclockwise position in which the syringes are aligned with this row as illustrated in FIG. 6. Bar 48, whose function is equivalent to that of pins 22 in the preceding embodiment, thus arrests the support 9' above the receptacle holder 26, 27 to let the descending plungers discharge the contents of the syringes into the row of receptacles aligned therewith.

Motor 40 also drives, through a speed reducer 41, a shaft 39 of a stepped cam 38 coacting with a roller 43 on carriage 23. Cam 38 has five planar dwells 42, separated by axial distances equal to the center spacing of adjacent receptacle rows, onto which the cam follower 43 is held by the weight of the carriage which may be supplemented by a restoring spring not shown. Cam 38 is so synchronized with cams 33 and 35 that carriage 23 takes one step after each refilling operation, advancing from a starting position $P_1$ (shown in full lines) into successive phantom-line positions $P_2$, $P_3$, $P_4$ and $P_5$ in which the syringes discharge their contents into the second, third, fourth and fifth rows of receptacles rather than into the first row as illustrated in FIG. 6. At the end of this cycle, the carriage 23 slides back into position $P_1$ while another set of receptacles takes the place of the one just filled.

I claim:

1. A machine for introducing measured amounts of liquids into a set of receptacles, comprising:
   a base carrying upwardly open container means filled with a supply of liquid;
   a mounting disposed above said base;
   an upper support and a lower support guided on said mounting for generally vertical reciprocation;
   a set of horizontally spaced-apart syringes with barrels carried on said lower support and with plungers carried on said upper support, said supports being provided with first retaining means for releasably holding said supports together to hold said plungers fully inserted into said barrels and being interconnected by a lost-motion linkage enabling limited separation of said supports to an extent sufficient for a partial withdrawal of said plungers from said barrels;
   operating means connected with said upper support for reciprocating same between a top position and a bottom position with entrainment of said lower support, said barrels dipping into said container means in said bottom position, said lower support and said base being provided with second retaining means capable or overriding said first retaining means for releasably holding said lower support onto said base during part of an ascending stroke of said upper support whereby some of the liquid in said container means is aspirated into said barrels by the rising plungers, said lost-motion linkage disengaging said lower support from said base and elevating the filled barrels during the remainder of said ascending stroke;
   holding means carrying receptacles alignable with the filled barrels in their elevated position; and
   stop means for keeping said lower support elevated during a subsequent descending stroke of said upper support whereby the contents of said barrels are discharged by said plungers into the receptacles aligned therewith.

2. A machine as defined in claim 1 wherein said mounting is a frame with a pair of columns traversing said supports.

3. A machine as defined in claim 1 wherein said first and second retaining means are a relatively weak and a relatively strong magnetic coupling.

4. A machine as defined in claim 1 wherein said holding means is interposable between said lower support and said base, said stop means comprising an extension on said lower support coming to rest on the interposed holding means.

5. A machine as defined in claim 1 wherein said lost-motion linkage comprises a threaded rod traversing said supports and a nut on said rod enabling adjustment of the maximum separation of said supports.

6. A machine as defined in claim 1 wherein said mounting is swingable about a horizontal axis for alternately aligning said barrels with said container means and with said holding means.

7. A machine as defined in claim 6 wherein said stop means comprises a brace articulated to said lower support and to said base for coming to rest on said holding means upon alignment of said barrels therewith.

8. A machine as defined in claim 6 wherein said operating means comprises first cam means for swinging said mounting about said axis and second cam means synchronized with said first cam means for reciprocating said upper support on said mounting.

9. A machine as defined in claim 8, further comprising spring means for holding a cam follower on said mounting engaged with said first cam means, said second cam means positively engaging a cam follower on said upper support.

10. A machine as defined in claim 8 wherein said recptacles are arrayed on said holding means in a plurality of rows parallel to said axis, further comprising a carriage pivotally supporting said mounting, said carriage being movable relatively to said holding means in a direction perpendicular to said rows, and drive means synchronized with said first and second cam means for successively aligning said barrels in their liquid-filled state with different rows of receptacles.

11. A machine as defined in claim 10 wherein said drive means comprises a stepped cam.

12. A machine as defined in claim 6 wherein said holding means includes a transporter advancing intermittently past said mounting, further comprising hopper means for successively depositing sets of receptacles on said transporter.

13. A machine as defined in claim 1 wherein said container means comprises at least one vessel divided into a main compartment and an overflow compartment, feed means terminating at said main compartment for continously supplying liquid thereto from a source, and drain means extending from said overflow compartment to said source.

14. A machine as defined in claim 13 wherein said feed means comprises a conduit provided with a fluid pump.

15. A machine as defined in claim 14 wherein said conduit is an upwardly open channel, said fluid pump comprising an endless conveyor carrying rollers received in said channel.

* * * * *